US 10,415,872 B2

(12) United States Patent
Kang et al.

(10) Patent No.: US 10,415,872 B2
(45) Date of Patent: Sep. 17, 2019

(54) INNER CABINET FOR REFRIGERATOR AND REFRIGERATOR INCLUDING THE SAME

(71) Applicant: Samsung Electronics Co., Ltd, Gyeonggi-do (KR)

(72) Inventors: Jung Hye Kang, Suwon-si (KR); Boo-Keun Yoon, Yongin-si (KR); Shang Hun Lee, Suwon-si (KR); Young Deog Koh, Seongnam-si (KR); Jin O Kwak, Suwon-si (KR); Bum Soo Kim, Yongin-si (KR); Geun Woo Park, Suwon-si (KR); Noh Cheol Park, Yongin-si (KR); In Soon Kang, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/860,465

(22) Filed: Jan. 2, 2018

(65) Prior Publication Data
US 2018/0187960 A1     Jul. 5, 2018

(30) Foreign Application Priority Data
Jan. 3, 2017     (KR) ........................ 10-2017-0000521

(51) Int. Cl.
*F25D 23/06*     (2006.01)
*C04B 33/24*     (2006.01)
(Continued)

(52) U.S. Cl.
CPC ............ *F25D 23/065* (2013.01); *A61L 9/012* (2013.01); *C04B 33/04* (2013.01); *C04B 33/24* (2013.01);
(Continued)

(58) Field of Classification Search
CPC ................ F25D 23/065; F25D 23/066; F25D 2325/022; C04B 38/0074
See application file for complete search history.

(56) References Cited

U.S. PATENT DOCUMENTS

| 4,168,334 A | * | 9/1979 | Crandall | ................ A21B 3/133 220/573.1 |
| 4,212,924 A | * | 7/1980 | Reed | ........................ C03C 8/08 428/428 |

(Continued)

FOREIGN PATENT DOCUMENTS

| JP | 2006199561 A | 8/2006 |
| JP | 2012172610 A | 9/2012 |

(Continued)

OTHER PUBLICATIONS

European Patent Office, "European Search Report," Application No. EP 17210034.9, dated Jul. 6, 2018, 10 pages.

(Continued)

*Primary Examiner* — Andrew M Roersma

(57) ABSTRACT

Embodiments of the present disclosure relate to an inner cabinet for a refrigerator formed of a ceramic material and a refrigerator including the same. One aspect of an inner cabinet for a refrigerator, the inner cabinet includes a ceramic material comprising at least one of silicon oxide and aluminum oxide as a main component, wherein the ceramic material has a ratio of an area occupied by pores per unit surface area in the range of 0.1 to 10%.

14 Claims, 9 Drawing Sheets

(51) Int. Cl.
*C04B 35/18* (2006.01)
*A61L 9/01* (2006.01)
*C04B 38/00* (2006.01)
*C04B 33/04* (2006.01)
*A61L 9/012* (2006.01)

(52) U.S. Cl.
CPC .......... *C04B 35/18* (2013.01); *C04B 38/0074* (2013.01); *F25D 23/066* (2013.01); *A61L 2209/22* (2013.01); *F25D 2325/022* (2013.01)

(56) References Cited

U.S. PATENT DOCUMENTS

| | | | | |
|---|---|---|---|---|
| 4,690,727 | A * | 9/1987 | Scott | C04B 35/115 134/2 |
| 5,422,318 | A * | 6/1995 | Hagg | C03C 10/0045 501/4 |
| 5,731,250 | A * | 3/1998 | Reid | C04B 35/481 501/106 |
| 6,165,590 | A * | 12/2000 | Takagi | C04B 41/009 428/152 |
| 2006/0057407 | A1 * | 3/2006 | Sambasivan | C03C 17/22 428/472.3 |
| 2007/0114897 | A1 * | 5/2007 | Neumann | A47B 96/021 312/408 |
| 2011/0127227 | A1 * | 6/2011 | Epp | F25D 25/02 211/133.6 |
| 2012/0177909 | A1 | 7/2012 | Uchino et al. | |
| 2012/0237745 | A1 * | 9/2012 | Dierkes | A61K 6/0215 428/215 |
| 2016/0281959 | A1 * | 9/2016 | Khizar | A47L 15/241 |
| 2018/0187958 | A1 * | 7/2018 | Kim | B32B 5/024 |

FOREIGN PATENT DOCUMENTS

| | | |
|---|---|---|
| JP | 2013242106 A | 12/2013 |
| JP | 2014119228 A | 6/2014 |
| KR | 20020001472 A | 1/2002 |
| KR | 20020094385 A | 12/2002 |
| KR | 10-2004-0089250 A | 10/2004 |
| KR | 10-2012-0111048 A | 10/2012 |
| KR | 10-2015-0038843 A | 4/2015 |

OTHER PUBLICATIONS

Database WPI, Week 200520, Thomson Scientific, London, GB, AN 2005-191286, XP-002777794, 1 page.
Database WPI, Week 201280, Thomson Scientific, London, GB, AN 2012-N46767, XP-002777795, 2 pages.
Database WPI, Week 201535, Thomson Scientific, London, GB, AN 2015-24800N, XP-002777796, 2 pages.
European Patent Office, "Communication under Rule 71(3) EPC," Application No. EP17210034.9, dated Dec. 19, 2018, 28 pages.

* cited by examiner

INNER CABINET FOR REGRIGERATOR AND REFRIGERATOR INCLUDING THE SAME

CROSS-REFERENCE TO RELATED APPLICATION(S)

This application is related to and claims priority to Korean Patent Application No. 10-2017-0000521 filed on Jan. 3, 2017, the disclosure of which is incorporated herein by reference.

TECHNICAL FIELD

Embodiments of the present disclosure relate to an inner cabinet for a refrigerator formed of a ceramic material and a refrigerator including the same.

BACKGROUND

Since various types of food are stored in a refrigerator, odors may be easily produced from the food stored in the refrigerator and bacteria may grow therein. As the period of use of the refrigerator increases, odors and bacteria have accumulated onto inner walls and it is difficult to remove the odors and bacteria. In addition, the odors and bacteria accumulated in the refrigerator may be transferred to newly stored food and thus convenience and reliability of the refrigerator may deteriorate.

Conventionally, inner cabinets of refrigerators have been fabricated using an acrylonitrile butadiene styrene (ABS) extruded sheet formed of an organic polymer by vacuum molding. Such inner cabinets fabricated in this manner have a non-uniform and rough surface formed during a vacuum molding process. As a result, odor molecules are adsorbed to injection-molded plastic surfaces so that chemical odors and food odors may remain therein.

In order to solve these problems, research has been conducted into various methods of maintaining the inside of the refrigerator in a clean state, for example, by using a coating composition applicable to the surface of the inner cabinet of the refrigerator.

SUMMARY

To address the above-discussed deficiencies, it is a primary object to provide an inner cabinet for a refrigerator having excellent image clarity with no residual color and residual odor by adjusting a porosity of a surface of a ceramic material and a refrigerator including the same.

Particularly, an inner cabinet for a refrigerator formed of a ceramic material having a porosity adjusted by glaze-coating the surface of the ceramic material and polishing the surface and a refrigerator including the same are provided.

Additional aspects of the disclosure will be set forth in part in the description which follows and, in part, will be obvious from the description, or may be learned by practice of the disclosure.

One aspect of present disclosure there is provided an inner cabinet for a refrigerator. The inner cabinet includes a ceramic material comprising at least one of silicon oxide and aluminum oxide as a main component, wherein the ceramic material has a ratio of an area occupied by pores per unit surface area in the range of 0.1 to 10%.

The ceramic material may comprise 35.6 to 62.5% by weight of silicon oxide and 13.2 to 34.4% by weight of aluminum oxide based on a total weight of the ceramic material.

The ceramic material may have an image clarity of 40 to 95.

The ceramic material may have a color difference value ($\Delta E$) of less than 0.5 in a food color reaction for residual color verification.

The ceramic material may have a glaze coating layer formed on the surface thereof.

The glaze coating layer may be surface-polished by using a diamond slurry.

The diamond slurry may have a particle diameter of 0.05 to 1.0 μm.

One aspect of present disclosure, there is provided a refrigerator. The refrigerator may comprise an inner cabinet having storage compartments formed therein; and an outer cabinet coupled to outer sides of the inner cabinet and defining an appearance, wherein the inner cabinet is formed of a ceramic material comprising at least one of silicon oxide and aluminum oxide as a main component, and the ceramic material has a ratio of an area occupied by pores per unit surface area in the range of 0.1 to 10%.

The ceramic material may comprise 35.6 to 62.5% by weight of silicon oxide and 13.2 to 34.4% by weight of aluminum oxide based on a total weight of the ceramic material.

The ceramic material may have an image clarity of 40 to 95.

The ceramic material has a color difference value ($\Delta E$) of less than 0.5 in a food color reaction for residual color verification.

The ceramic material may have a glaze coating layer formed on the surface thereof.

The glaze coating layer may be surface-polished by using a diamond slurry.

The diamond slurry may have a particle diameter of 0.05 to 1.0 μm.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
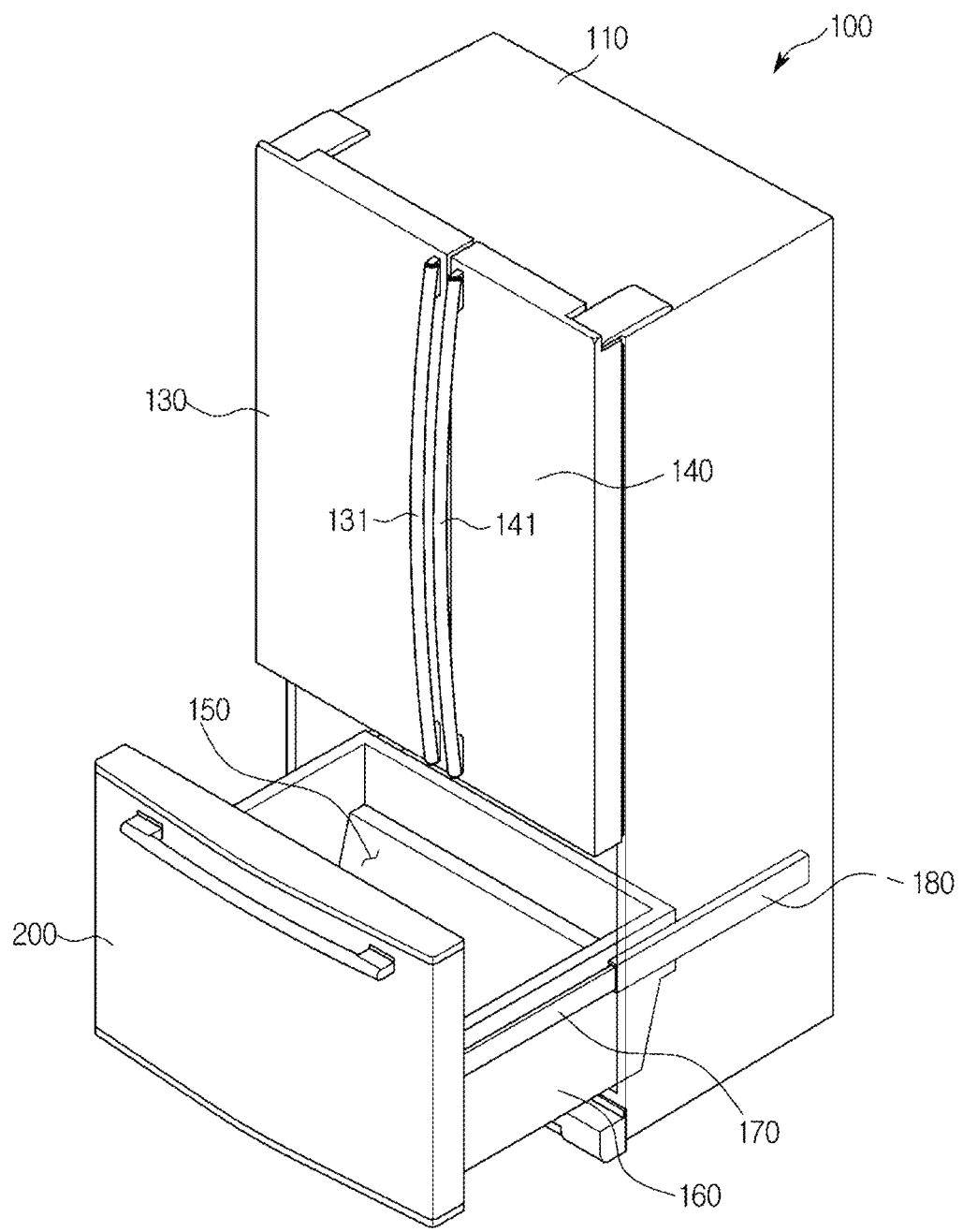
FIG. 1 is a perspective view illustrating an appearance of a refrigerator 100 according to an embodiment.

FIGS. 1 through 9, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Reference will now be made in detail to the embodiments of the present disclosure, examples of which are illustrated in the accompanying drawings, wherein like reference numerals refer to like elements throughout. This specification does not describe all elements of the embodiments of the present disclosure and detailed descriptions on what are well known in the art or redundant descriptions on substantially the same configurations may be omitted.

Also, it is to be understood that the terms "include" or "have" are intended to indicate the existence of elements disclosed in the specification, and are not intended to preclude the possibility that one or more other elements may exist or may be added.

Throughout the specification, it will be understood that when one element, is referred to as being "on" another element, it can be directly on the other element, or intervening elements may also be present there between.

In this specification, terms "first," "second," etc. are used to distinguish one component from other components and, therefore, the components are not limited by the terms.

An expression used in the singular encompasses the expression of the plural, unless it has a clearly different meaning in the context.

Hereinafter, operating principles and embodiments of the present disclosure will be described with reference to the accompanying drawings.

Figure 2:
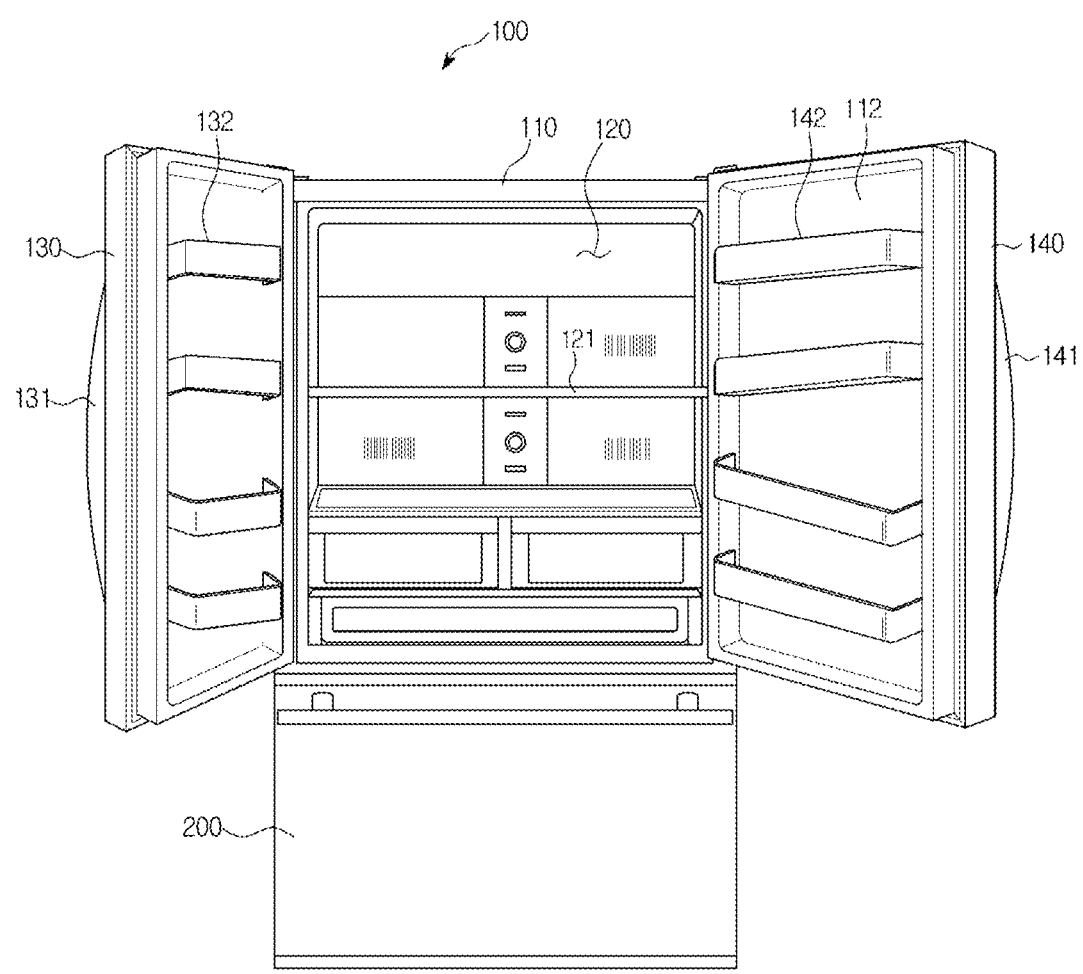
FIG. 2 is a view illustrating the inside of the refrigerator 100.

FIG. 1 is a perspective view illustrating an appearance of a refrigerator 100 according to an embodiment. FIG. 2 is a view illustrating the inside of the refrigerator 100.

Referring to FIGS. 1 and 2, the refrigerator 100 may include a main body 110, storage compartments 120 and 150 formed in the main body 110, storage compartment doors 130, 140, and 200 rotatably coupled to a front surface of the main body 110 and configured to shield the insides of the storage compartments 120 and 150 from the outside, and a cool air supply device (not shown) configured to supply cool air to the storage compartments 120 and 150.

The main body 110 may include an inner cabinet 112 defining the storage compartments 120 and 150, an outer cabinet coupled to outer surfaces of the inner cabinet 112, and an insulation material disposed between the inner cabinet 112 and the outer cabinet to prevent an outflow of cool air from the storage compartments 120 and 150 and an inflow of external warm air into the storage compartments 120 and 150.

A machine room may be disposed at a lower portion of the main body 110. Components such as a compressor are accommodated in the machine room and a refrigerant may be compressed at a high temperature and a high pressure by the compressor.

The storage compartments 120 and 150 may be partitioned into an upper refrigerator compartment 120 and a lower freezer compartment 150 by an intermediate wall. The refrigerator compartment 120 may be maintained at about 3° C., and the freezer compartment 150 may be maintained at about −18° C.

The refrigerator compartment 120 has an open front to store food. The open front may be opened or closed by a pair of refrigerator compartment doors 130 and 140 pivotally coupled thereto by using hinge members (not shown). The refrigerator compartment doors 130 and 140 include a left door 130 configured to open or close a left part of the refrigerator compartment 120 and a right door 140 configured to open or close a right part of the refrigerator compartment 120. The refrigerator compartment 120 may include shelves 121 on which food is placed.

Refrigerator compartment door handles 131 and 141 used to open or close the refrigerator compartment doors 130 and 140 may be provided at front surfaces of the refrigerator compartment doors 130 and 140. The refrigerator compartment door handles 131 and 141 may include a left door handle 131 used to open the left part of the refrigerator compartment 120 and a right door handle 141 used to open the right part of the refrigerator compartment 140. Also, door guards 132 and 142 on which food is placed may be provided at rear surfaces of the refrigerator compartment doors 130 and 140. The door guards 132 and 142 may include a left door guard 132 disposed at the rear surface of the left door 130 and a right door guard 142 disposed at the rear surface of the right door 140.

The freezer compartment 150 may have an open front to store food. The open front may be opened or closed by a freezer compartment door 200 sliding forward and backward. A storage box 160 may be disposed at a rear surface of the freezer compartment door 200.

The freezer compartment door 200 and the storage box 160 may be provided with movable rail units 170, and the movable rail unit 170 may be slidably supported by fixed rail units 180 disposed at the main body 110. Thus, the freezer compartment door 200 and the storage box 160 may slide into and out of the main body 110. A freezer compartment door handle used to open or close the freezer compartment door 200 may be disposed at the front surface of the freezer compartment door 200.

The cool air supply device may include a compressor to compress the refrigerant, a condenser (not shown) to condense the refrigerant, a capillary pipe (not shown) to expand the refrigerant, and an evaporator (not shown) to generate cool air by evaporating the refrigerant.

An example of the structure of the refrigerator 100 according to the present disclosure has been described above. However, the structure of the refrigerator 100 is not limited to those illustrated in FIGS. 1 and 2 and may also be understood as a concept including modifications obvious to those skilled in the art.

Hereinafter, a material used to form the inner cabinet of the refrigerator 100 illustrated in FIGS. 1 and 2 will be described in detail. The inner cabinet of the refrigerator may be formed of a ceramic material. The ceramic material is used to impart excellent image clarity to the surface of the inner cabinet 112 of the refrigerator 100. By adjusting a ratio of pores formed on the surface of the ceramic material, residual odor and residual color caused by food stored in the refrigerator 100 may be minimized. Hereinafter, the ceramic material used to manufacture the inner cabinet 112 of the refrigerator 100 according to an embodiment will be described in detail.

The ceramic material includes a pottery material and a porcelain material prepared by compression-heating clay and minerals at a temperature of about 1000° C. to about 1400° C. Natural raw materials such as quartz, feldspar, and pottery-stone may be used as the minerals, but examples of the minerals are not limited thereto. Since natural materials such as clay and minerals are used as the ceramic material according to an embodiment, reactions between harmful substances derived from plastics with food components may be minimized during storage of food so that the food may be stored more safely.

The ceramic material may include at least one of silicon oxide and aluminum oxide as a main component. For example, the ceramic material may include 35.6 to 62.5% by weight of silicon oxide and 13.2 to 34.4% by weight of aluminum oxide based on a total weight of the ceramic material.

According to the present embodiment, a phenomenon in which inner walls of the refrigerator 100 are colored by contaminants generated by food stored in the refrigerator 100 may be prevented by adjusting a ratio of an area occupied by pores per unit surface area of the ceramic material. Hereinafter, the ratio of an area occupied by pores per unit surface area of the ceramic material will be referred to as porosity.

For example, a ceramic material having a porosity of 0.1 to 10% may be used to manufacture the inner cabinet 112 for a refrigerator according to an embodiment. When the ratio of pores per unit surface area of the ceramic material is adjusted as described above, the ceramic material used to form the inner cabinet may have an image clarity of about 40 to 95 and a color difference value (ΔE) of less than 0.5 in a food color reaction for residual color verification. The color difference value of the food color reaction for residual color verification was measured after brining the ceramic material into contact Kimchi for 24 hours and removing Kimchi therefrom.

In other words, by minimizing of the ratio of an area occupied by pores per unit surface area of the ceramic material used to form the inner cabinet 112 of the refrigerator 100, a phenomenon in which odor molecules, and the like are adhered to inner walls of the refrigerator 100 may be minimized and contaminants adhered to the inner walls of the refrigerator may be easily removed.

Meanwhile, when the porosity of the ceramic material is greater than 10%, residual color and residual odor may be caused by food stored in the refrigerator. Thus, the porosity of the ceramic material may be appropriately adjusted so as to provide a ceramic material having properties according to a designer's intended purpose.

The ceramic material may include a glaze coating layer formed on the surface thereof to realize the porosity described above. The glaze coating layer may be formed in such a manner that the surface of the ceramic material is subjected to a glaze coating process, followed by drying and polishing.

Hereinafter, a process of forming a glaze coating layer on the surface of the ceramic material to obtain a desired porosity will be described in detail for better understanding. However, the following manufacturing process is an example of forming the glaze coating layer and the technical idea of the present disclosure is not limited to the manufacturing process described below.

A method of realizing the desired porosity on the surface of the ceramic material is as follows.

First, a pottery or porcelain ceramic material having a thickness of 3.0 mm or greater is prepared. Then, the surface of the ceramic material is coated with a glaze to a thickness of 500 μm and burned at a temperature of 1100° C. higher for 100 minutes or more to prepare a non-porous surface.

The prepared surface is uneven and has an image clarity of 50 or less. According to the present disclosure, after drying the coated glaze, the glaze coating layer is polished in order to provide excellent image clarity to the surface of the inner cabinet of the refrigerator, thereby realizing a ceramic-like feeling and texture. A polishing process is performed to improve image clarity of the surface of the ceramic material. The porosity of the surface of the ceramic material may be adjusted by controlling types of an abrasive and an amount of polishing.

A surface plate polishing device was used to perform the polishing process according to an embodiment. Upper and lower surface plates of the surface plate polishing device were pressed under a pressure of about 0.1 to 0.5 kgf while fixing an RPM of the upper surface plate to 10 rpm, an RPM of the lower surface plate to 20 rpm, and weights of both of the upper and lower surface plates to 150 kg. Then, the glaze coating layer was polished by about 500 nm at a rate of 0.003 μm/min.

Also, a diamond slurry was used as the abrasive. The diamond slurry is a material having higher hardness than the ceramic material. In order to realize a mirror-like surface by polishing the surface of the ceramic material, the diamond slurry was selected as the abrasive.

A diamond slurry having a particle diameter of 0.05 to 1.0 μm was used. When the particle diameter of the diamond slurry is greater than 1.0 μm, the porosity of the surface of the ceramic material is greater than 10%. When the ceramic material having a porosity greater than 10% is applied to the inner cabinet 112 of the refrigerator, color and odor may remain in the inner cabinet 112 of the refrigerator. Thus, the particle diameter of the diamond slurry may be appropriately adjusted in accordance with specifications of a desired ceramic material.

Meanwhile, types of the abrasive are not limited to the diamond slurry and any other abrasives having higher hardness than the ceramic material may also be used.

When the ceramic material prepared as described above is applied to the inner cabinet 112 of the refrigerator, an inner cabinet 112 of the refrigerator having excellent image clarity with no residual color and odors and a refrigerator including the same may be provided. Thus, food may be stored in a fresh state for a long period of time and contaminants adhered to the surface of the inner cabinet 112 of the refrigerator may be easily removed so that the refrigerator may be easily cleaned.

Hereinafter, the behavior of odor molecules on the surface of the ceramic material prepared as described above will be described.

Figure 3:
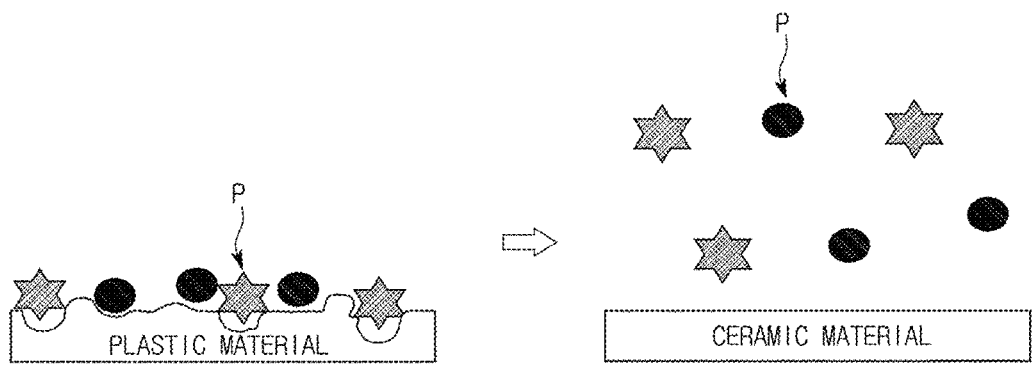
FIG. 3 is a diagram illustrating the behavior of odor molecules P on surfaces of a plastic material and a ceramic material.
Figure 4:
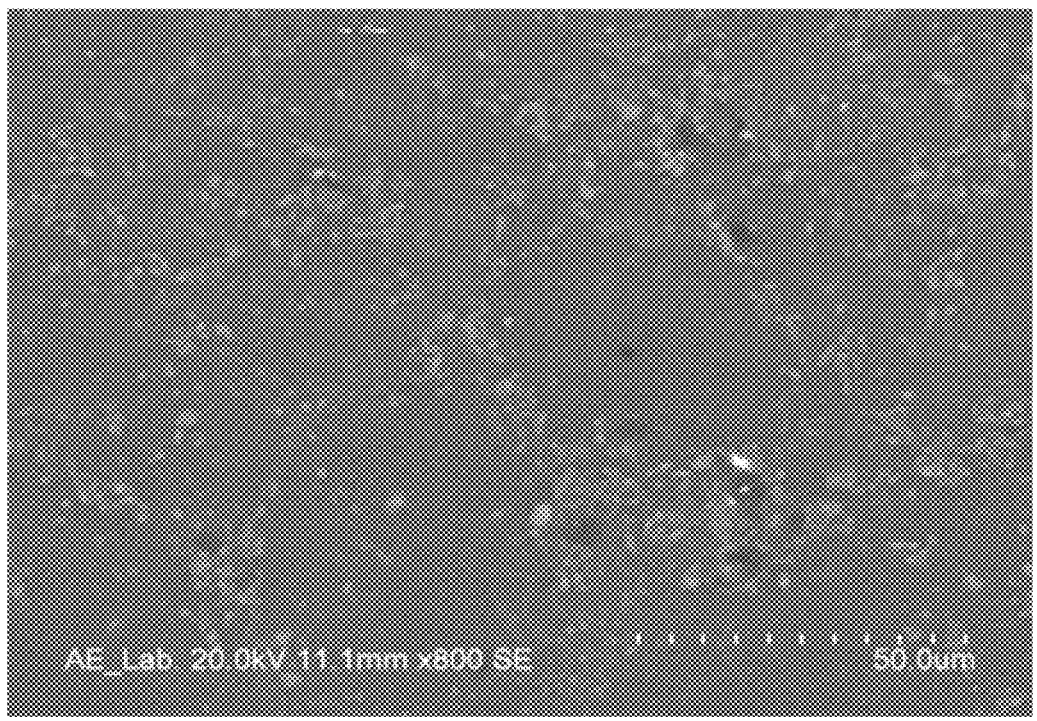
FIGS. 4 to 9 are photographs of pores on surfaces of the ceramic materials prepared according to Examples 1 and 2 and Comparative Examples 1 to 4.
Figure 5:
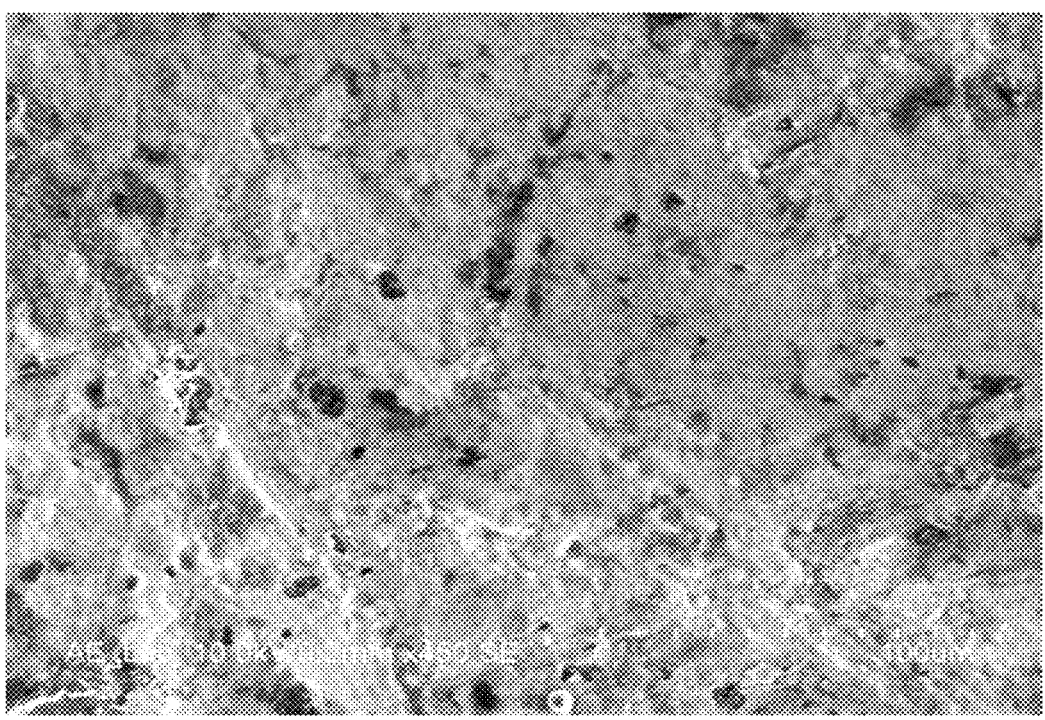
Figure 6:
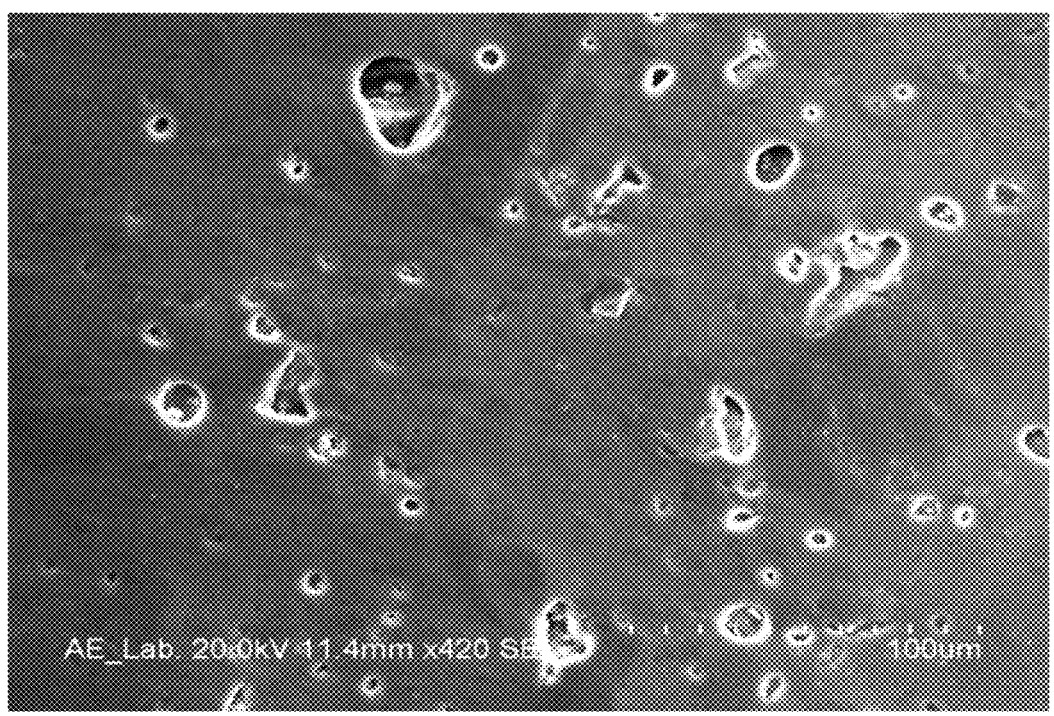
Figure 7:
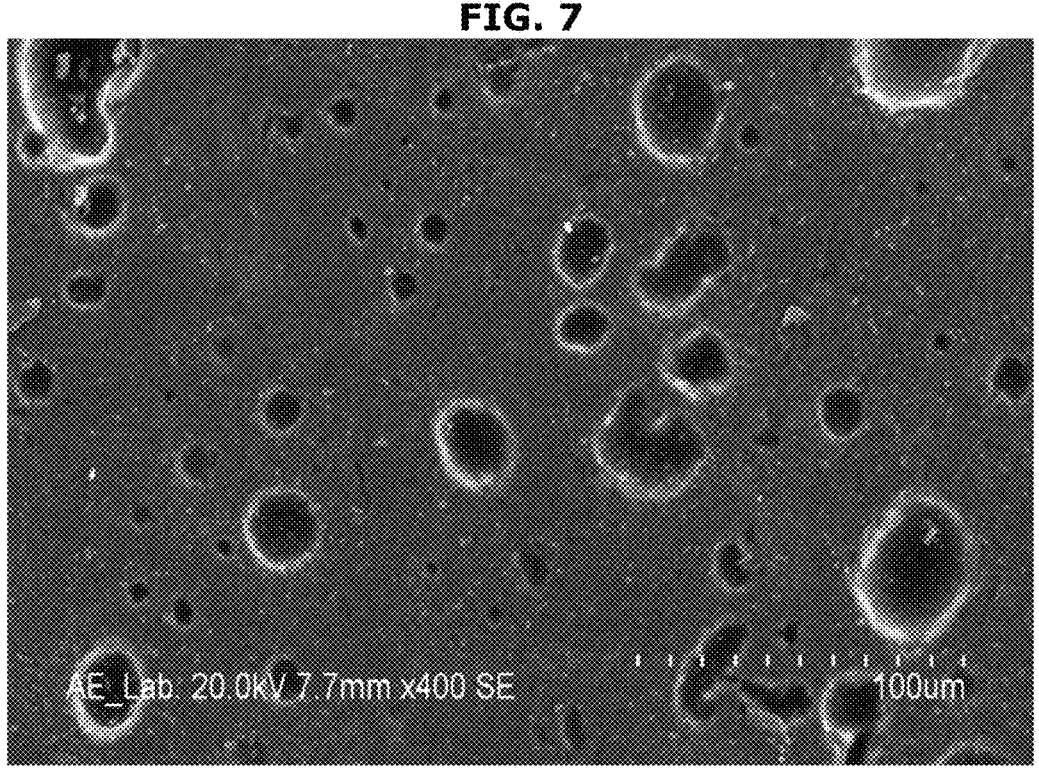
Figure 8:
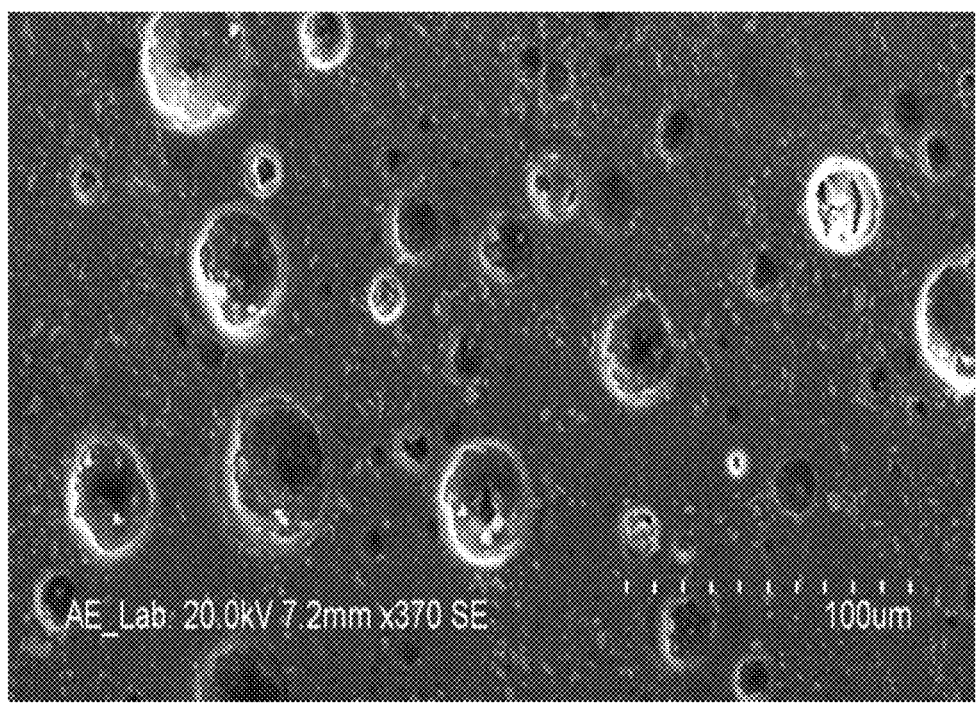
Figure 9:
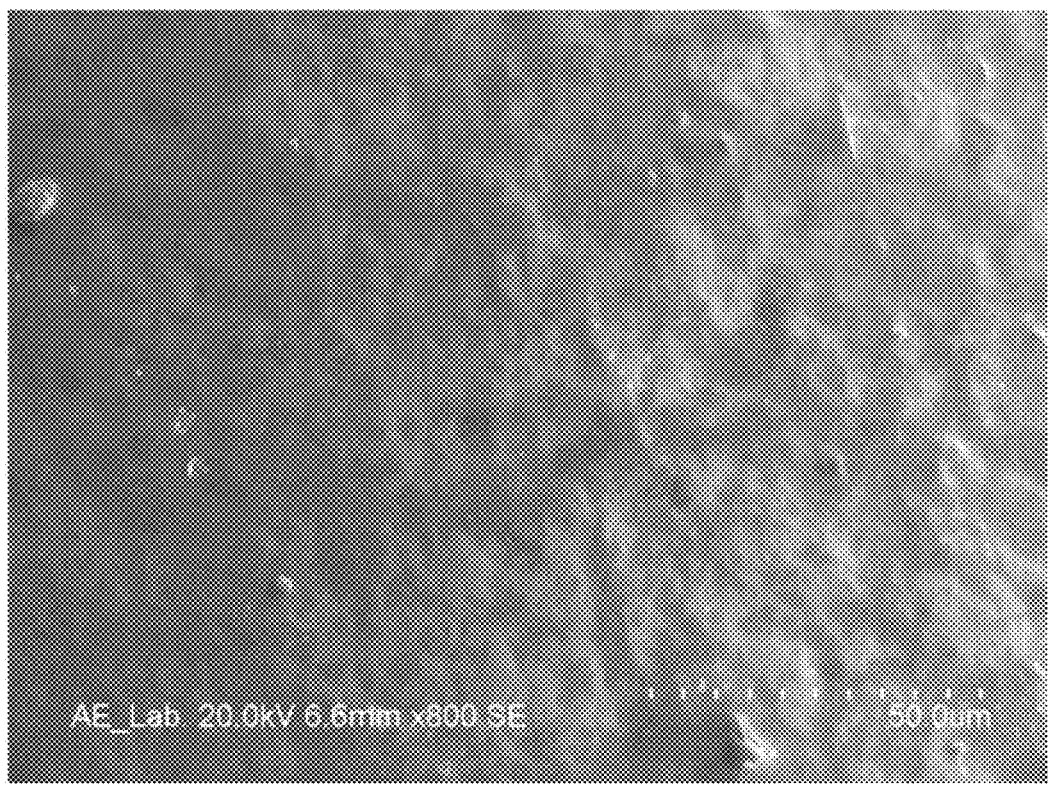

FIG. 3 is a diagram illustrating the behavior of odor molecules P on surfaces of a plastic material and a ceramic material.

Referring to FIG. 3, the plastic material has an uneven and rough surface as compared with that of the ceramic material according to an embodiment. Thus, odor molecules P and the like derived from food stored in the refrigerator are more easily adsorbed to the plastic material. When the plastic material is applied to a refrigerator, deodorizing performance may deteriorate.

Actually, in an inner cabinet of a refrigerator to which a conventional ABS material is applied, chemical odors or food odors always remain by 5 to 8% due to properties of the material. Even when a deodorizer operates, deodorization cannot be performed by 100%.

On the contrary, the ceramic material according to an embodiment has a porosity of about 0.1 to 10% thereby having a uniform and dense surface, Thus, odor molecules cannot be adsorbed to the surface of the ceramic material, so that odors may not remain therein. When the ceramic material is applied to the inner cabinet of the refrigerator, excellent deodorizing performance may be achieved.

In addition, since the ceramic material is formed of natural raw materials such as clay and ore as main components, harmful substances derived from plastics do not react with food ingredients while storing food so that the food may be stored more safely and internal cleanliness of the refrigerator may be improved.

Next, experimental results of characteristics of the ceramic material according to the present embodiment with respect to types of the abrasive used while polishing the ceramic material will be described to assist in a further understanding of the invention.

In these experiments, cases according to Examples 1 to 2 and Comparative Examples 1 to 4 were designed to measure characteristics of the ceramic material with respect to the particle diameter of the diamond slurry as the abrasive.

Example 1

According to Example 1, a ceramic material having a thickness of 3.0 mm was coated with a glaze to a thickness of 500 μm and burned at a temperature of 1100° C. or higher for 100 minutes or longer to form a non-porous surface. Then, the coated surface was dried for a predetermined time and subjected to a polishing process.

The polishing process was performed by using a surface plate polishing device. Specifically, about 500 nm of the glaze-coated surface was polished at a rate of 0.003 μm/min while fixing an RPM of the upper surface plate to 10 rpm, an RPM of the lower surface plate to 20 rpm, and weights of both of the upper and lower surface plates to 150 kg and pressing the upper and lower surface plates at a pressure of about 0.1 to 0.5 kgf. A diamond slurry having a particle diameter of 0.05 to 0.25 μm was used as an abrasive during the polishing process.

Example 2

According to Example 2, the polishing process was performed by using a diamond slurry having a particle diameter of 0.5 to 1.0 μm. The other processes are the same as those of Example 1.

Comparative Example 1

According to Comparative Example 1, the polishing process was performed by using a diamond slurry having a particle diameter of 9.0 to 15 μm. The other processes are the same as those of Example 1.

Comparative Example 2

According to Comparative Example 2, the polishing process was performed by using a diamond slurry having a particle diameter of 30 μm. The other processes are the same as those of Example 1.

Comparative Example 3

According to Comparative Example 3, the polishing process was performed by using a diamond slurry having a particle diameter of 45 μm. The other processes are the same as those of Example 1.

Comparative Example 4

According to Comparative Example 4, a ceramic material having a thickness of 3.0 mm was coated with a glaze to a thickness of 500 μm and burned at a temperature of 1100° C. or higher for 100 minutes or longer to form a non-porous surface. The ceramic material was not subjected to a polishing process.

In this experiment, a ceramic material was prepared to satisfy an image clarity of 40 to 95, a porosity of 10% or less, a residual color of less than 0.5 (ΔE), and no residual odor (0%).

Porosities and physical properties of ceramic materials prepared according to Examples 1 and 2 and Comparative Examples 1 to 4 are shown in Table 1 below.

TABLE 1

|  | Example 1 | Example 2 | Comparative Example 1 | Comparative Example 2 | Comparative Example 3 | Comparative Example 4 |
| --- | --- | --- | --- | --- | --- | --- |
| Image clarity | 43.2-48.5 | 62.9-69.9 | 71.4-77.7 | 82.5-88.4 | 83.4-89.2 | 26.3-32.8 |
| Porosity (%) | 1.1-1.7 | 2.8-8 | 14.5-20.2 | 31.6-40.5 | 55.5-65.0 | 0 |
| Residual color (ΔE) | 0.19 | 0.4 | 0.75 | 1.1 | 2.8 | 0.08 |
| Residual odor (%) | 0 | 0 | 5 | 13 | 15 | 0 |

FIGS. 4 to 9 are photographs of pores on surfaces of the ceramic materials prepared according to Examples 1 and 2 and Comparative Examples 1 to 4.

Referring to Table 1 and FIGS. 4 to 9, the following conclusions may be deduced.

First, when the polishing processes were performed according to Examples 1 and 2 and Comparative Examples 1 to 3, it was confirmed that the ceramic materials having an image clarity of 40 or greater were prepared as compared with the case according to Comparative Example 4 in which the polishing process was not performed.

Meanwhile, it was confirmed that the porosity of the ceramic material increased as the particle diameter of the diamond slurry increased based on the experiments according to Comparative Examples 1 to 3. Specifically, in the case of Comparative Example 1 where the diamond slurry having a particle diameter of 9 to 15 μm was used, it was confirmed that the ceramic material had a porosity of about 14.5 to 20.2%. In the case of Comparative Example 2 where the diamond slurry having a particle diameter of 30 μm was used, it was confirmed that the ceramic material had a porosity of about 31.6 to 40.5%. In the case of Comparative Example 3 where the diamond slurry having a particle diameter of 45 µm was used, it was confirmed that the ceramic material had a porosity of about 55.5 to 65.0%.

On the contrary, in the case of Example 1 where the diamond slurry having a particle diameter of 0.05 to 0.25 µm was used, it was confirmed that the ceramic material had a porosity of about 1.1 to 1.7%. In the case of Example 2 where the diamond slurry having a particle diameter of 0.5 to 1.0 µm was used, it was confirmed that the ceramic material had a porosity of about 2.8 to 8%.

According to the present disclosure, residual color and residual odor may be minimized by adjusting the surface porosity of the ceramic material to 10% or less. Referring to Table 1, as the surface porosity of the ceramic material increase, it may be confirmed that residual color and residual odor increase. Thus, it may be confirmed that the particle diameter of the diamond slurry needs to be adjusted in the range of about 0.05 to 1.0 µm.

As is apparent from the above description, according to the present disclosure, an inner cabinet for a refrigerator having excellent image clarity with no residual color and odor and a refrigerator including the same may be provided.

Particularly, by using a material having excellent image clarity to fabricate the inner cabinet of the refrigerator, the inner cabinet may have a ceramic-like texture and improved design.

In addition, by using a material causing no residual color and no residual odor to fabricate the inner cabinet, food may be stored in a fresh state for a long period of time. Also, contaminants adhered to the surface of the inner cabinet of the refrigerator may be easily removed so that the refrigerator may be more easily cleaned.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An inner cabinet for a refrigerator, the inner cabinet comprising:
    a ceramic material comprising at least one of silicon oxide and aluminum oxide as a main component,
    wherein the ceramic material has a ratio of an area occupied by pores per unit surface area in the range of 0.1 to 10%.

2. The inner cabinet for a refrigerator of claim 1, wherein the ceramic material comprises 35.6 to 62.5% by weight of silicon oxide and 13.2 to 34.4% by weight of aluminum oxide based on a total weight of the ceramic material.

3. The inner cabinet for a refrigerator of claim 1, wherein the ceramic material has an image clarity of 40 to 95.

4. The inner cabinet for a refrigerator of claim 1, wherein the ceramic material has a color difference value ($\Delta E$) of less than 0.5 in a food color reaction for residual color verification.

5. The inner cabinet for a refrigerator of claim 1, wherein the ceramic material has a glaze coating layer formed on the surface thereof.

6. The inner cabinet for a refrigerator of claim 5, wherein the glaze coating layer is surface-polished by using a diamond slurry.

7. The inner cabinet for a refrigerator of claim 6, wherein the diamond slurry has a particle diameter of 0.05 to 1.0 µm.

8. A refrigerator comprising:
    an inner cabinet having storage compartments formed therein; and
    an outer cabinet coupled to outer sides of the inner cabinet and defining an appearance,
    wherein the inner cabinet is formed of a ceramic material comprising at least one of silicon oxide and aluminum oxide as a main component, and
    the ceramic material has a ratio of an area occupied by pores per unit surface area in the range of 0.1 to 10%.

9. The refrigerator of claim 8, wherein the ceramic material comprises 35.6 to 62.5% by weight of silicon oxide and 13.2 to 34.4% by weight of aluminum oxide based on a total weight of the ceramic material.

10. The refrigerator of claim 8, wherein the ceramic material has an image clarity of 40 to 95.

11. The refrigerator of claim 8, wherein the ceramic material has a color difference value ($\Delta E$) of less than 0.5 in a food color reaction for residual color verification.

12. The refrigerator of claim 8, wherein the ceramic material has a glaze coating layer formed on the surface thereof.

13. The refrigerator of claim 12, wherein the glaze coating layer is surface-polished by using a diamond slurry.

14. The refrigerator of claim 13, wherein the diamond slurry has a particle diameter of 0.05 to 1.0 µm.

* * * * *